US010568760B2

(12) United States Patent
Paradis

(10) Patent No.: US 10,568,760 B2
(45) Date of Patent: Feb. 25, 2020

(54) METHOD TO DETECT CHANGES IN A PATIENT'S ENDOGENOUS TEMPERATURE SET-POINT DURING EXTERNALLY INDUCED TARGETED TEMPERATURE MANAGEMENT

(71) Applicant: ZOLL Circulation Inc., San Jose, CA (US)

(72) Inventor: Norman A. Paradis, Putney, VT (US)

(73) Assignee: Zoll Circulation, Inc., San Jose, CA (US)

( * ) Notice: Subject to any disclaimer, the term of this patent is extended or adjusted under 35 U.S.C. 154(b) by 143 days.

(21) Appl. No.: 14/642,259

(22) Filed: Mar. 9, 2015

(65) Prior Publication Data

US 2015/0250643 A1    Sep. 10, 2015

Related U.S. Application Data

(60) Provisional application No. 61/950,294, filed on Mar. 10, 2014.

(51) Int. Cl.
*A61F 7/00*    (2006.01)

(52) U.S. Cl.
CPC .... *A61F 7/0085* (2013.01); *A61F 2007/0054* (2013.01); *A61F 2007/0094* (2013.01); *A61F 2007/0095* (2013.01)

(58) Field of Classification Search
CPC ...... A61F 2007/0054; A61F 2007/0094; A61F 2007/0095; A61F 7/0085; A61F 7/02; A61F 2007/0093
See application file for complete search history.

(56) References Cited

U.S. PATENT DOCUMENTS

| | | | |
|---|---|---|---|
| 8,696,725 B2 | 4/2014 | Kulstad et al. | |
| 2006/0122673 A1* | 6/2006 | Callister | A61F 7/12 607/105 |
| 2013/0030411 A1* | 1/2013 | Kreck | A61F 7/12 604/514 |
| 2014/0213843 A1 | 7/2014 | Pilla et al. | |
| 2015/0105687 A1 | 4/2015 | Abreu | |
| 2015/0250643 A1 | 9/2015 | Paradis | |
| 2016/0331244 A1 | 11/2016 | Barton-Sweeney | |

FOREIGN PATENT DOCUMENTS

WO    WO 2015/168228 A1    11/2015

OTHER PUBLICATIONS

Van Ooijen, A.M.J., et al., "Cold-induced heat production preceding shivering." British Journal of Nutrition 93 (2005), pp. 387-391.

(Continued)

*Primary Examiner* — Kaitlyn E Smith
*Assistant Examiner* — Tigist S Demie
(74) *Attorney, Agent, or Firm* — Fish & Richardson P.C.

(57) ABSTRACT

A method for utilizing heat transfer parameters or energy expenditure of devices providing controlled hypothermia, normothermia or hyperthermia to detect changes, or the absence of changes, a patient's endogenous set-point temperature; which is not available during exogenously induced targeted temperature management. A particular embodiment would allow detection of fever in patients undergoing targeted temperature managed.

22 Claims, 1 Drawing Sheet

(56) References Cited

OTHER PUBLICATIONS

Gaieski, D.F., et al., "Impact of time to antibiotics on survival in patients with severe sepsis or septic shock in whom early goal-directed therapy was initiated in the emergency department." Grit. Care Med, vol. 38, No. 3 (2010), pp. 1045-1053.

Holzer, M., "Targeted temperature management for comatose survivors of cardiac arrest." N. Engl. J. Med, vol. 363, No. 13 (2010), pp. 1256-1264.

Tanabe, S., et al., Evaluation of thermal comfort using combined multi-node thermoregulation (65MN) and radiation models and computational fluid dynamics (CFD). Energy and Buildings 34 (2002), pp. 637-646.

Mekjavic, I.B., and Eiken, O., "Contribution of thermal and nonthermal factors to the regulation of body temperature in humans." J. Appl. Physiol. 1985, vol. 100, No. 6 (2006), pp. 2065-2072.

Akata, T., et al., "Reliability of fingertip skin-surface temperature and its related thermal measures as indices of peripheral perfusion in the clinical setting of the operating theatre." Anaesthesia and Intensive Care, vol. 32 (2004), pp. 519-529.

Knapik, P., et al., "Comparison of intravascular and conventional hypothermia after cardiac arrest." Kardiologia Polska 69 (2011), pp. 1157-1164.

David M. Greer, et al., "Impact of Fever on Outcome in Patients with Stroke and Neurologic Injury," Stroke, Oct. 27, 2008, vol. 39, pp. 3029-3035, http://stroke.ahajournals.org/content/39/11/3029.

Extended European Search Report in Application No. 17776507, dated Nov. 4, 2019, 7 pages.

\* cited by examiner

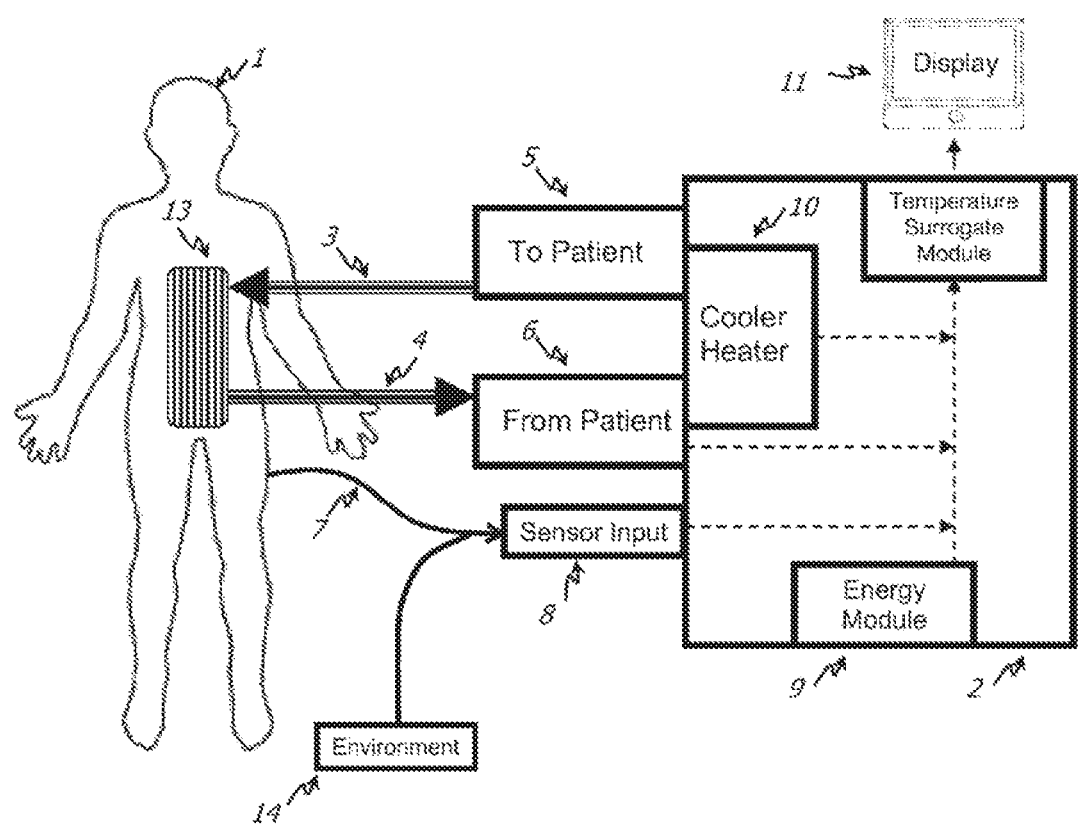

METHOD TO DETECT CHANGES IN A PATIENT'S ENDOGENOUS TEMPERATURE SET-POINT DURING EXTERNALLY INDUCED TARGETED TEMPERATURE MANAGEMENT

CLAIM OF PRIORITY

This patent application claims benefit to U.S. Provisional Patent Application Ser. No. 61/950,294 filed Mar. 10, 2014 by Norman A. Paradis for a METHOD FOR UTILIZING ENERGY EXPENDITURE OR HEAT TRANSFER PARAMETERS OF DEVICES PROVIDING CONTROLLED HYPOTHERMIA, NORMOTHERMIA OR HYPERTHERMIA AS A SURROGATE FOR PATIENT TEMPERATURE, which patent application is hereby incorporated herein by reference.

FIELD OF THE INVENTION

The invention disclosed herein relates in general to the field of medical devices used for exogenous temperature management, and more particularly, to a method for utilizing measurements of thermal transfer or energy expenditure of such devices as a surrogate for the patient's endogenous temperature status, which is not available during exogenously induced targeted temperature management.

BACKGROUND OF THE INVENTION

Endogenous patient set-point temperature is a function of a complex afferent system that senses environmental and endogenous needs for alterations of physiologic set-point temperature, and an efferent effector system that alters physiologic energy output through processes such as shivering and decoupling of mitochondrial respiration. (Crawshaw et al. 19-30) The organ of central importance in establishing the physiologic set-point temperature is the hypothalamus, a region of brain that interfaces between the central nervous and endocrine systems.

Measurement of a patient's endogenous temperature set-point is very important clinically and it is one of the classic vital signs. It is generally considered the most important early indicator of infection. Early diagnosis and treatment are the most important predictors of outcome in serious infection. (Gaieski et al. 1045-53)

In medicine, targeted temperature management, hereinafter referred to as TTM, is the artificial induction and maintenance of a specific core body temperature as a treatment for a disease or adjunct to another therapy. The temperature induced and maintained may be hypothermic, normothermic, or hyperthermic. Hypothermia is a subnormal body temperature (below approximately 37.6° C.). Normothermia is a normal body temperature (approximately 37.0°±0.4° C.). Hyperthermia or hyperpyrexia is a supranormal body temperature (above approximately 37.4° C.).

Hypothermic, normothermic and hyperthermia, TTM are becoming increasingly important in the medical management of various disease states. For instance, therapeutic hypothermia is utilized in preventing organ injury in diseases such as cardiac arrest, stroke and acute myocardial infarction. Artificial exogenously induced hypothermia is commonly used to treat coma after cardiac arrest. (Holzer 1256-64)

Hypothermia may have clinical utility in any disease state that includes ischemia-reperfusion or acute inflammation as a component of its pathophysiology. It is also utilized in the treatment of brain injury. Controlled normothermia and prevention of hyperthermia are also potentially effective in the treatment of ischemia-reperfusion. Further, therapeutic hyperthermia may be important in improving the efficacy of drugs such as cancer chemotherapy agents and in the treatment of infection.

There are a number of methods for inducing and maintaining hypothermic, normothermic, or hyperthermic TTM. A typical TTM device is comprised of a subsystem to affect heat transfer between the TTM device and a patient, sensing and control mechanisms for managing the heat transfer, and a heating-cooling unit.

The subsystem to affect heat transfer may include one or more components, such as a catheter, a blanket or adhesive pads, and a heat-transfer fluid. The components of this subsystem are generally designed to optimize the efficiency of heat transfer, and may utilize a temperature-controlled fluid, such as water or saline, supplied to one or more components, such as a catheter, a blanket or an adhesive pad.

The control subsystems generally utilize negative feedback mechanisms. When an event occurs wherein the patient's temperature deviates from the intended target temperature, the event is detected by the sensing subsystem. The heating-cooling and heat transfer subsystems are then adjusted so as to return the patient's temperature to the target temperature. To avoid oscillation, the control system may include feed-forward and dampening algorithms.

The control system is generally computer based, and may be comprised of a sensing subsystem, feedback control and dampening mechanisms, and interfaces with the heat-transfer and heating-cooling subsystems. Standard electrical devices, generally incorporating circuit boards, semiconductor chips and transistors, are available to perform these functions.

The sensing subsystem will generally incorporate a thermometer or thermistor within or upon the patient and a electrical connection to the control subsystem.

The heating-cooling unit of a typical TTM device is generally a variation on widely available heating and refrigeration devices.

While TTM may improve the outcome of patient suffering from various disease states, it makes the patient's endogenous set-point temperature an important clinical vital sign unavailable to the clinicians caring for the patient. Depending on the responsiveness, power and sophistication of the device providing TTM, the patient's measurable temperature may deviate from the target temperature by an amount that is not detectable by clinicians.

Inability to detect changes in a patient's endogenous set-point temperature can have negative effects on the clinical outcome of patients. The inflammation that heralds the onset of an infection is normally detected by the onset of fever. The inability to detect changes in the patient's endogenous temperature set-point may delay the detection of a fever and subsequent diagnosis and treatment of an infection. It is currently believed that the single most important determinant of outcome in life threatening infection is the time from onset of infection to initiation of therapy with appropriate antibiotics.

In general, TTM will mask, or make more difficult to detect, endogenous temperature changes when patients suffer infection or other disease states that are associated with an alteration in the endogenous temperature set-point. Sepsis, for instance, is often associated with endogenous hypothermia. Failure to detect the endogenous hypothermia may delay the diagnosis of sepsis leading to a worse outcome.

It is common during TTM to administer drugs that induce neuromuscular blockade along with appropriate sedation. These medications will assist in temperature control but will also act to mask or completely ablate shivering. This renders the detection of fever onset more difficult.

DESCRIPTION OF THE RELATED ART

It has not been generally appreciated that the temperature vital sign is not available during TTM. Consequently, prior to this disclosure, it has not been clearly understood by clinicians that patients undergoing TTM will not manifest a fever, and that this may delay diagnosis of infection and other alterations in clinical status.
The following comprehensive searches of the World Wide Web found no results:
"detecting fever during hypothermia"
"detecting fever during induced hypothermia"
"detecting fever during targeted temperature management"
"diagnosis of fever during hypothermia"
"diagnosis of fever during induced hypothermia"
"diagnosis of fever during targeted temperature management"
"diagnosis of infection during targeted temperature management"
"diagnosis of pneumonia during hypothermia"
"diagnosis of pneumonia during induced hypothermia"
"diagnosis of pneumonia during targeted temperature management"
"masks fever during hypothermia"
"detecting fever during hypothermia"
As would be expected in light of the failure to appreciate the absence of measurable changes in a patient's endogenous set-point temperature, and thus clinically apparent fever, during TTM, there is no prior art teaching the use of device derived energy and heat transfer parameters as surrogates for these important clinical parameters.
The following comprehensive searches of the World Wide Web found no results:
"surrogate for temperature during hypothermia"
"surrogate for temperature during induced hypothermia"
"surrogate for temperature during targeted temperature management"
"alternative(s) for temperature during targeted temperature management"
"alternative(s) for temperature during hypothermia"
"changes in temperature during hypothermia"
"changes in temperature during induced hypothermia"
"changes in temperature during targeted temperature management"
"changes in patient temperature during targeted temperature management"
Summary of Deficiencies in the Prior Art
1) There has been no prior appreciation that TTM masks fever. For instance, a comprehensive review of TTM after cardiac arrest describes infection as an adverse event, yet fails to address the absence of detectable fever. (Holzer 1256-64)
2) There has been no prior appreciation that the energy or heat transfer parameters of the TTM device may substitute for changes in endogenous temperature set-point.
These and other components, features and advantages of the present invention will become clearer when the drawings as well as the detailed description are taken into consideration.

Usefulness of the Disclosed Invention
Once it is understood that the invention disclosed herein restores the ability of clinicians to detect, diagnose, and treat diseases associated with changes in endogenous set-point temperature, the usefulness will be obvious to anyone with ordinary skill in the art. In particular, it will be useful in the diagnosis of fever and infection in patients undergoing external cooling. This would allow earlier administration of antibiotics, which would be associated with improved patient outcomes.
Non-Obviousness
The non-obviousness of the invention herein disclosed is demonstrated by the complete absence of its description in either the patent, medical, or technical literature. Additionally, a number of large commercial enterprises produce devices for the induction and maintenance of TTM; despite extensive research and development effort, none of these companies have disclosed or developed methods or systems such as disclosed herein.
The development and improvement of TTM and its associated technology has received significant effort from clinicians and biomedical device companies. Companies in particular are motivated to distinguish their systems from those of their competitors. If the use of the energy or heat transfer parameters of the TTM device as a surrogate for changes in endogenous temperature set-point, or their use in early diagnosis of fever and infection, were in any manner obvious, they would have been described previously.

SUMMARY OF THE INVENTION

What has been Invented?
The present disclosure is for a method or system intended generally to detect fever, defervescence, or absence of either, in patients undergoing TTM. The method encompassing measurement, transformation, and presentation of the energy or thermal requirements needed to maintain the patient at a specific target temperature. Alternatively, a algorithmic combination of the thermal input or output, temperature of the cooling/heating transfer subsystem, along with environment temperature, and patient specifics, may be utilized.

BRIEF DESCRIPTION OF THE DRAWINGS

For a fuller understanding of the nature of the present invention, reference should be made to the following detailed description taken in connection with the accompanying drawings in which:
FIG. 1 is a diagrammatic representation of one embodiment of the method.

DETAILED DESCRIPTION OF A PREFERRED EMBODIMENT

A practitioner skilled in the art would, once taught the invention, appreciate that during TTM, the measured patient temperature will no longer be a useful indicator of a patient's endogenous set-point temperature. However, a change in the patient's endogenous temperature set-point may be detected as a change in: 1) the energy required by the heat-cooling subsystem, such as cooler/heater 10 to maintain the therapeutically targeted temperature, 2) the volume and/or temperature of the heat-transfer fluid 3, 3) the energy expenditure of the heat-cooling subsystem such as a cooler/heater 10, or a combination of these.
A change in the patient's endogenous temperature regulation and set-point, might also first be detected by a change in the temperature of fluid 4 being returned to the TTM device 2.

As an example of the clinical application of the invention—when the TTM device is being utilized for maintenance of controlled hypothermia or normothermia, the onset of fever in a patient will be detectable as a need to provide additional cold, or colder, fluid, to the heat-exchange subsystem 13 and an associated increase in the energy being drawn through energy module 9 by the heat-cooling subsystem, such as a cooler/heater 10. The abatement of fever, defervescence, would be detected by the opposite of these events.

Similarly, when the TTM device is being utilized for maintenance of controlled hyperthermia, the onset of fever in a patient will be detectable as a need to provide less warm fluid 3 to the heat-exchange subsystem 13 and an associated decrease in the energy expenditure of the TTM device. Again, the abatement of fever would be detected by the opposite of these events.

The changing requirements for cooler or warmer heat transfer fluid at the onset of infection and fever, and the associated difference in the energy requirement of the TTM device 2, may be presented as data to assist clinicians. Further, the different requirements to provide cold or warm fluid or the difference in the energy required by the TTM device could be plotted against time, or change from baseline, and displayed graphically on display 11.

The different requirements to provide cooler or warmer fluid or the difference in the energy required by the TTM device may be combined with other data, for e.g. measurements of metabolism or physiology, to derive an earlier or more accurate assessment of a patient's endogenous temperature regulation.

The different requirements to provide cooler or warmer fluid 3 or the difference in the energy required by the TIM 2 device may, with or without combination with other data, be utilized in an algorithm to predict impending shivering and deploying counter-shivering therapies. These therapies may include control of the TIM device itself to alter the speed with which alteration in TTM are effected.

It is generally recognized brat presentation of physiologic data graphed against time assist clinicians in the diagnosis and management of disease. The different requirements to provide cooler or warmer fluid, or the difference in the energy required by the TTM device to maintain the therapeutic target temperature may, with or without combination with other data, be presented visually to assist clinicians. Particular embodiments of this visual presentation may include, but are not limited to, the variables as a function of time or change from baseline.

To improve the accuracy of the system in detecting changes in patient endogenous set-point temperature, the environment temperature 14, or changes in the environment temperature 14, may be incorporated into the algorithm utilized.

Someone of ordinary skill in the art, once taught the invention, would understand that conversion of measured energy expenditure or transfer fluid temperature to an artificial surrogate for changes in patient temperature is a variant of classic heat transfer:

$$Q = mc\Delta T$$

Heat transfer=(mass)(specific heat)(temperature change)

Q=heat content in Joules
m=mass
c=specific heat
T=temperature
ΔT=change in temperature Inclusion of a general purpose computer within the system would allow solution of this problem. Utilization of more advanced nonlinear and multivariable models would likely be associated with improved performance in the algorithms utilized.

Mode that May be Constructed by Someone Skilled in the Art

By way of example, but not limitation, a mode that would be easily constructed by someone skilled in the art would include:

1. A component that measures the temperatures and volumes of the fluid utilized by the heat transfer subsystem of the device providing TTM. Techniques for measurement of temperature are well know and include thermometers, thermistors, and infrared detectors, among others. Techniques for measurement of fluid flow are also well know and include flow meters of various design. Standard electrical devices, generally incorporating circuit boards, semiconductor chips and transistors, are available to perform these functions.

2. A component that measures the energy utilized by the cooling or warming subsystem of the device providing TTM. Standard electrical devices, generally incorporating circuit boards, semiconductor chips and transistors, along with thermistors, are available to perform the necessary functions.

3. A component that transforms said measurements into a clinically useful surrogate representative of the patient's endogenous set-point temperature and changes in this parameter over time. The latter would function as a surrogate diagnostic of fever. These results may be presented graphically. Standard electrical devices, generally incorporating circuit boards, semiconductor chips and transistors, along with a general purpose computer and video presentation technology, are available to perform these functions.

Methods for the derivation of a multivariable algorithm for detection of changes in endogenous set-point temperature based on measurements of fluid transfer temperatures, fluid transfer volumes, heating or cooling energy requirements, or a combination of these parameters, would be well known to a practitioner of ordinary skill in heat transfer and mathematical modeling.

Modifications

It will be understood that many changes in the details, materials, steps and arrangements of elements, which have been herein described and illustrated in order to explain the nature of the invention, may be made by those skilled in the art without departing from the scope of the present invention.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

OTHER PUBLICATIONS INCORPORATED IN THE CURRENT APPLICATION BY REFERENCE

Crawshaw, L., et al. "Central nervous regulation of body temperature in vertebrates: comparative aspects." *Pharmacol. Ther.* 30.1 (1985): 19-30.

Gaieski, D. F., et al. "Impact of time to antibiotics on survival in patients with severe sepsis or septic shock in whom early goal-directed therapy was initiated in the emergency department." *Crit Care Med.* 38.4 (2010): 1045-53.

Holzer, M. "Targeted temperature management for comatose survivors of cardiac arrest." *N. Engl. J. Med.* 363.13 (2010): 1256-64.

Now that the invention has been described,

What is claimed is:

1. A method comprising:
measuring an amount of heat being gained or lost by a heat transfer fluid as it circulates through a body heat exchange subsystem of a targeted temperature control device that is maintaining a patient body temperature at a target temperature; and
determining whether a change in the measured amount of heat being gained or lost indicates that an endogenous thermoregulatory mechanism of the patient is seeking to raise or lower said patient body temperature but is prevented from doing so because said patient body temperature is being maintained at said target temperature by said targeted temperature control device.

2. A method according to claim 1 wherein the determining, step comprises:
measuring an amount of energy utilized by targeted temperature management device to warm or cool the heat transfer fluid in order to maintain said body temperature at said target temperature.

3. A method according to claim 1 wherein the determining step comprises:
determining changes in an amount of heat transfer fluid that must be circulated through the body heat exchange subsystem to maintain said body temperature at the target temperature.

4. A method according to claim 1 wherein the determining step comprises:
determining changes in the amount of heat that the targeted temperature management device must add to or remove from the heat transfer fluid to maintain said body temperature at the target temperature.

5. A method according to claim 1 wherein the determining step comprises:
equating a magnitude of change in the measured amount of heat being gained or lost by the heat transfer fluid as it circulates through the body heat exchange subsystem with an expected body temperature that would presently be attained if said body temperature were not being maintained at said target temperature by the targeted temperature management device.

6. A method according to claim 5 wherein said equating step comprises:
using a mathematical formula to calculate said expected body temperature based on the magnitude of change in the measured amount of heat being gained or lost by the heat transfer fluid as it circulates through the body heat exchange subsystem as well as one or more other variables selected from: i) patient body mass and ii) the presence of, absence of, or change in a patient biomarker.

7. A method according to claim 5 wherein the targeted temperature management device includes a processor programmed to perform the equating step and wherein the equating step is performed by said processor.

8. A method according to claim 1 wherein the targeted temperature management device includes a display and wherein the method further comprises:
causing the display to display a clinically useful indicia of changes in a patient's endogenous thermoregulatory set point temperature.

9. A method according to claim 8 wherein the display provides a graphic display of an estimated endogenous thermoregulatory set point temperature of the patient as a function of time, magnitude of change from baseline, or both.

10. A method comprising:
measuring changes in an amount of heat being added to or removed from a patient's body by a targeted temperature management device in order to hold a body temperature of the patient at a target temperature;
using the measured changes in the amount of heat being added to or removed from the patient's body to calculate corresponding changes which would be expected to occur in said body temperature if said body temperature were not being held said a target temperature by the targeted temperature management device;
providing notice of said calculated corresponding changes.

11. A method according to claim 10 wherein the step of measuring changes in the amount of heat being added to or removed from the patient's body by the targeted temperature management device in order to hold said body temperature at said target temperature comprises at least one of: i) determining a difference in temperature of heat exchange fluid flowing into a body heat exchange subsystem of the targeted temperature management device and heat exchange fluid flowing out of that body heat exchange subsystem; ii) determining changes in flowrate of heat exchange fluid being circulated through the body heat exchange subsystem; and iii) determining changes in an amount of energy expended by the targeted temperature management device to maintain the target body temperature.

12. A method according to claim 10 wherein the using step comprises applying a mathematical formula to calculate said corresponding changes which would be expected to occur in said body temperature based on a) a magnitude of the measured changes in the amount of heat being added to or removed from the patient's body taking into account contemporaneous changes in one or more other variables selected from: i) patient body mass and ii) a presence of, absence of, or change in a patient biomarker.

13. A method according to claim 10 wherein the temperature management device includes a display and wherein, the step of providing notice of said calculated corresponding changes comprises causing the display to display an indication of change in an endogenous set point temperature of the patient as a function of time, magnitude of change from baseline, or both.

14. A method according to claim 10 wherein the temperature management device includes a processor programmed to perform the equating and providing steps.

15. A targeted temperature management system useable to maintain a body temperature of a patient at or within a permissible range of a target temperature, said system comprising:
a body heat exchange subsystem positionable on or in the body of said patient;
extracorporeal heat exchange apparatus for warming or cooling a heat exchange fluid;
a first flow path for carrying warmed or cooled beat exchange fluid from the extracorporeal heat exchange apparatus into the body heat exchange subsystem;

a second flow path for returning the heat exchange fluid from the body heat exchange subsystem back to the extracorporeal heat exchange apparatus;

a pump for circulating the heat exchange fluid from the extracorporeal heat exchange apparatus, through the first flow path, through the body heat exchange subsystem, through the second flow path and back to the extracorporeal heat exchange apparatus;

apparatus for measuring an amount of heat being added to or removed from the patient's body by the targeted temperature management device in order, to maintain the patient's actual body temperature at or within said the permissible range of the target temperature;

a body temperature sensor for sensing a body temperature;

a display; and a processor which, during operation of the system, receives signals from the apparatus for measuring said amount of heat being added to or removed from the patient's body and is programmed to a) determine whether those signals indicate that an endogenous thermoregulatory mechanism of the patient is seeking to raise or lower said body temperature but has not done so because said body temperature is being maintained at or within said permissible range of said target temperature by the body heat exchange subsystem, and b) cause the display to display an indication of that determination.

16. A system according to claim 15 wherein the apparatus for measuring the amount of heat being added to or removed from the patient's body is selected from i) apparatus for measuring a difference between a temperature of heat exchange fluid flowing into the body heat exchanger and a temperature heat exchange fluid flowing out of the body heat exchange subsystem; ii) apparatus for measuring changes in the amount of heat exchange fluid being circulated through the body heat exchange subsystem; and iii) apparatus for measuring changes in an amount of energy expended by the targeted temperature management system to maintain the body temperature of said patient at or within said permissible range of said target temperature.

17. A system according to claim 15 wherein the processor is programmed to determine whether said measured changes in the amount of heat being added to or removed from the patient's body indicate that an endogenous thermoregulatory mechanism of the patient is seeking to raise or lower said body temperature based on a) the magnitude of the determined change in the amount of heat being gained or lost by the heat transfer fluid and b) one or more other variables selected from: i) patient body mass and ii) the presence of, absence of, or change in a patient biomarker.

18. A system according to claim 15 wherein the processor is programmed to cause the display to display an expected body temperature that would be present if the temperature management system were not maintaining said body temperature at or within said permissible range of said target body temperature.

19. A system according to claim 15 wherein the body heat exchange subsystem comprises a heat exchange catheter.

20. A system according to claim 14 wherein the body heat exchange subsystem comprises a blanket or adhesive pad.

21. A method according to claim 1 wherein said target temperature comprises a temperature range.

22. A method according to claim 10 wherein said target temperature comprises a temperature range.

* * * * *

UNITED STATES PATENT AND TRADEMARK OFFICE
CERTIFICATE OF CORRECTION

PATENT NO. : 10,568,760 B2
APPLICATION NO. : 14/642259
DATED : February 25, 2020
INVENTOR(S) : Paradis It is certified that error appears in the above-identified patent and that said Letters Patent is hereby corrected as shown below:

In the Claims

Column 7, Lines 24-25, Claim 2, delete "determining," and insert -- determining --

Column 8, Line 19, Claim 10, before "said", insert -- at --

Column 8, Line 19, Claim 10, delete "a target" and insert -- target --

Column 8, Line 32, Claim 11, delete "in" and insert -- in a --

Column 8, Line 48, Claim 13, delete "wherein," and insert -- wherein --

Column 8, Line 65, Claim 15, delete "beat" and insert -- heat --

Column 9, Line 11, Claim 15, delete "order," and insert -- order --

Column 10, Line 27, Claim 20, delete "system" and insert -- method --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*